US012562003B2

(12) United States Patent
Nistico

(10) Patent No.: US 12,562,003 B2
(45) Date of Patent: Feb. 24, 2026

(54) PUPIL ASSESSMENT USING MODULATED ON-AXIS ILLUMINATION

(71) Applicant: APPLE INC., Cupertino, CA (US)

(72) Inventor: Walter Nistico, Redwood City, CA (US)

(73) Assignee: Apple Inc., Cupertino, CA (US)

( * ) Notice: Subject to any disclaimer, the term of this patent is extended or adjusted under 35 U.S.C. 154(b) by 893 days.

(21) Appl. No.: 17/411,163

(22) Filed: Aug. 25, 2021

(65) Prior Publication Data

US 2021/0378509 A1 Dec. 9, 2021

Related U.S. Application Data

(63) Continuation of application No. PCT/US2020/045562, filed on Aug. 10, 2020.

(Continued)

(51) Int. Cl.
*A61B 3/11* (2006.01)
*A61B 3/00* (2006.01)
(Continued)

(52) U.S. Cl.
CPC ............ *G06V 40/19* (2022.01); *A61B 3/0008* (2013.01); *A61B 3/112* (2013.01); *A61B 3/113* (2013.01);
(Continued)

(58) Field of Classification Search
CPC ....... A61B 3/0008; A61B 3/112; A61B 3/113; G06V 10/141; G06V 10/145; G06V 10/147; G06V 40/19
See application file for complete search history.

(56) References Cited

U.S. PATENT DOCUMENTS 4,519,685 A 5/1985 Momiyama et al.
6,154,321 A 11/2000 Melville
(Continued)

FOREIGN PATENT DOCUMENTS

CN 1725976 A 1/2006
CN 109715047 A 5/2019

OTHER PUBLICATIONS

European Patent Office (ISA/EP), International Search Report and Written Opinion of the International Searching Authority, International Application No. PCT/US2020/045562, 14 pages, Nov. 27, 2020.

(Continued)

*Primary Examiner* — Jack Dinh
(74) *Attorney, Agent, or Firm* — Thompson Hine LLP

(57) ABSTRACT

Various implementations determine a pupil characteristic (e.g., perimeter location, pupil shape, pupil diameter, pupil center, etc.) using on-axis illumination. On-axis illumination involves producing light from a light source that is approximately on-axis with an image sensor configured to capture reflections of the light from the light source off the eye. The light from the light source may passes through the pupil into the eye and reflect off the retina to produce a bright pupil-type light pattern in data obtained by the image sensor. The light may be pulsed at a frequency so that frequency segmentation may be used to distinguish reflections through the pupil off the retina from reflections of light from other light sources. In some implementations, the image sensor is an event camera that detects events. The pupil characteristics may be assessed by assessing events that recur in a given area at the given frequency.

18 Claims, 8 Drawing Sheets

Related U.S. Application Data

(60) Provisional application No. 62/887,761, filed on Aug. 16, 2019.

(51) Int. Cl.

| | |
|---|---|
| *A61B 3/113* | (2006.01) |
| *G02B 27/01* | (2006.01) |
| *G06V 10/141* | (2022.01) |
| *G06V 10/145* | (2022.01) |
| *G06V 10/147* | (2022.01) |
| *G06V 40/19* | (2022.01) |

(52) U.S. Cl.
CPC ....... *G02B 27/0172* (2013.01); *G06V 10/141* (2022.01); *G06V 10/145* (2022.01); *G06V 10/147* (2022.01)

(56) References Cited

U.S. PATENT DOCUMENTS

| | | | |
|---|---|---|---|
| 6,369,953 | B2 | 4/2002 | Melville |
| 6,916,096 | B2 | 7/2005 | Eberl |
| 7,262,919 | B1 | 8/2007 | Yamazaki |
| 8,177,408 | B1 | 5/2012 | Coleman |
| 9,360,935 | B2 | 6/2016 | Chan |
| 9,494,799 | B2 | 11/2016 | Robbins |
| 9,521,950 | B2 | 12/2016 | Verdooner |
| 9,661,215 | B2 | 5/2017 | Sivan |
| 9,866,748 | B2 | 1/2018 | Sivan |
| 10,073,518 | B2 | 9/2018 | Rahman |
| 10,423,222 | B2 | 9/2019 | Popovich |
| 10,432,922 | B2 | 10/2019 | Jarc |
| 10,687,703 | B2 | 6/2020 | Berestka et al. |
| 10,795,435 | B2 | 10/2020 | Fontanel et al. |
| 11,112,865 | B1 | 9/2021 | Fix |
| 11,828,946 | B2 | 11/2023 | Meitav |
| 11,966,047 | B2 | 4/2024 | Arvidsson |
| 12,260,560 | B1 | 3/2025 | Hazra |
| 2002/0036750 | A1 | 3/2002 | Eberl |
| 2009/0238051 | A1 | 9/2009 | Nishiwaki et al. |
| 2011/0176110 | A1 | 7/2011 | Bublitz |
| 2013/0012364 | A1 | 1/2013 | Leath |

| | | | |
|---|---|---|---|
| 2013/0128364 | A1 | 5/2013 | Wheeler |
| 2014/0009367 | A1 | 1/2014 | Lvovskiy |
| 2014/0375541 | A1 | 12/2014 | Nister |
| 2015/0035744 | A1 | 2/2015 | Robbins |
| 2015/0049013 | A1 | 2/2015 | Rahman |
| 2015/0199006 | A1 | 7/2015 | He et al. |
| 2016/0021303 | A1 | 1/2016 | Sutton |
| 2016/0041384 | A1 | 2/2016 | Robbins |
| 2016/0150219 | A1 | 5/2016 | Gordon |
| 2016/0307372 | A1 | 10/2016 | Pitts |
| 2017/0147859 | A1 | 5/2017 | Zhang |
| 2017/0237897 | A1 | 8/2017 | Sivan |
| 2017/0261750 | A1 | 9/2017 | Wong |
| 2018/0068449 | A1 | 3/2018 | Malaika et al. |
| 2018/0173303 | A1 | 6/2018 | Liu |
| 2019/0056600 | A1 | 2/2019 | Danziger |
| 2019/0101767 | A1 | 4/2019 | Geng |
| 2019/0235248 | A1 | 8/2019 | Ollila et al. |
| 2019/0250704 | A1 | 8/2019 | Price et al. |
| 2020/0020561 | A1 | 1/2020 | Benaissa |
| 2020/0241308 | A1 | 7/2020 | Danziger et al. |
| 2020/0355929 | A1 | 11/2020 | Zhang |
| 2020/0386919 | A1 | 12/2020 | Arima et al. |
| 2021/0041291 | A1 | 2/2021 | Liu |
| 2021/0093193 | A1 | 4/2021 | Birkner et al. |
| 2021/0232216 | A1 | 7/2021 | Hudman |
| 2021/0294106 | A1 | 9/2021 | Meitav |
| 2022/0010942 | A1 | 1/2022 | Cornelissen et al. |
| 2022/0229293 | A1 | 7/2022 | Xu |
| 2022/0261076 | A1 | 8/2022 | Choi |
| 2022/0341114 | A1 | 10/2022 | Shibayama |
| 2023/0061056 | A1 | 3/2023 | Shin et al. |
| 2023/0087535 | A1 | 3/2023 | Sharma |
| 2023/0333213 | A1 | 10/2023 | Cadugan |
| 2023/0367117 | A1 | 11/2023 | Afek |

OTHER PUBLICATIONS

Borsato, F.H. et al., "A Fast and Accurate Eye Tracker Using Stroboscopic Differential Lighting," 2015 IEEE International Conference on Computer Vision Workshop, IEEE, pp. 502-510, Dec. 2015.

China National Intellectual Property Administration, Notification of the First Office Action with English translation, Chinese Patent Application No. 2020800576310, 19 pages, Apr. 29, 2025.

100

Controller 110

Physical
Setting 105

120

Controller 110

Memory 220

Operating System 230

Experience Module 240

Data Obtainer 242

Tracker 244

Coordinator 246

Renderer 248

Comm. Interface(s) 208

Programming Interface(s) 210

CPU(s) 202

I/O Device(s) 206

204

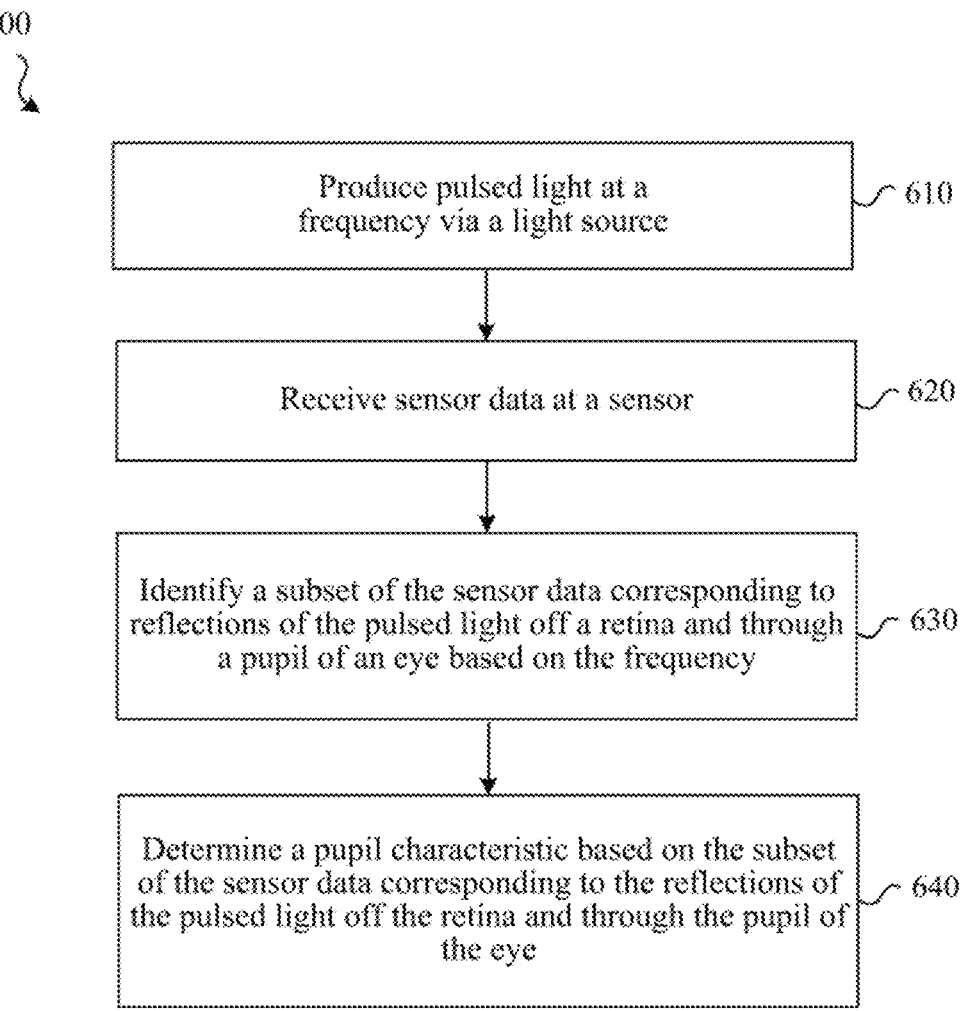

600

Produce pulsed light at a
frequency via a light source — 610

Receive sensor data at a sensor — 620

Identify a subset of the sensor data corresponding to
reflections of the pulsed light off a retina and through — 630
a pupil of an eye based on the frequency Determine a pupil characteristic based on the subset
of the sensor data corresponding to the reflections of — 640
the pulsed light off the retina and through the pupil of
the eye

FIG. 6

BRIGHT PUPIL EFFECT
"Off-axis" Illumination
Dark pupil effect
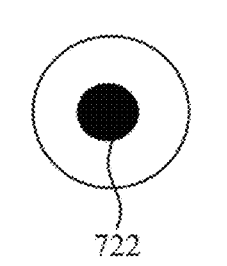
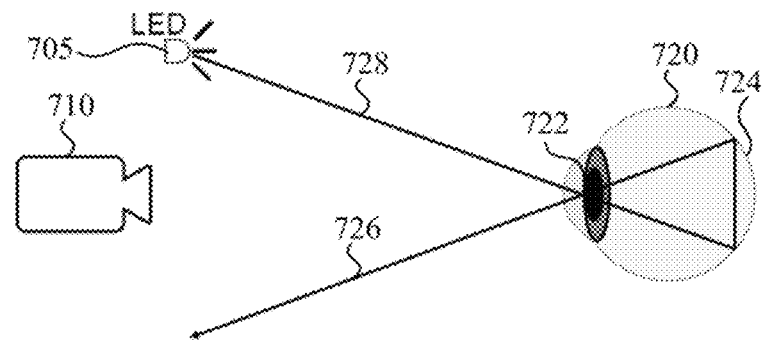
Bright pupil effect
"On-axis" Illumination
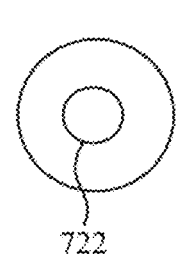
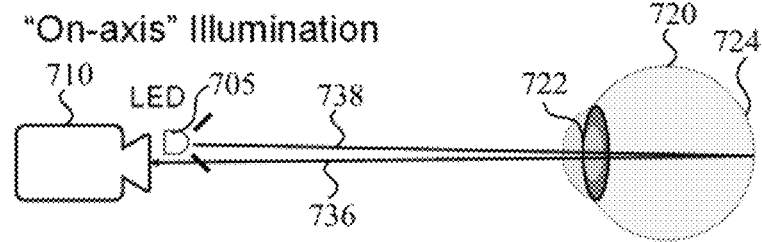
FIG. 7

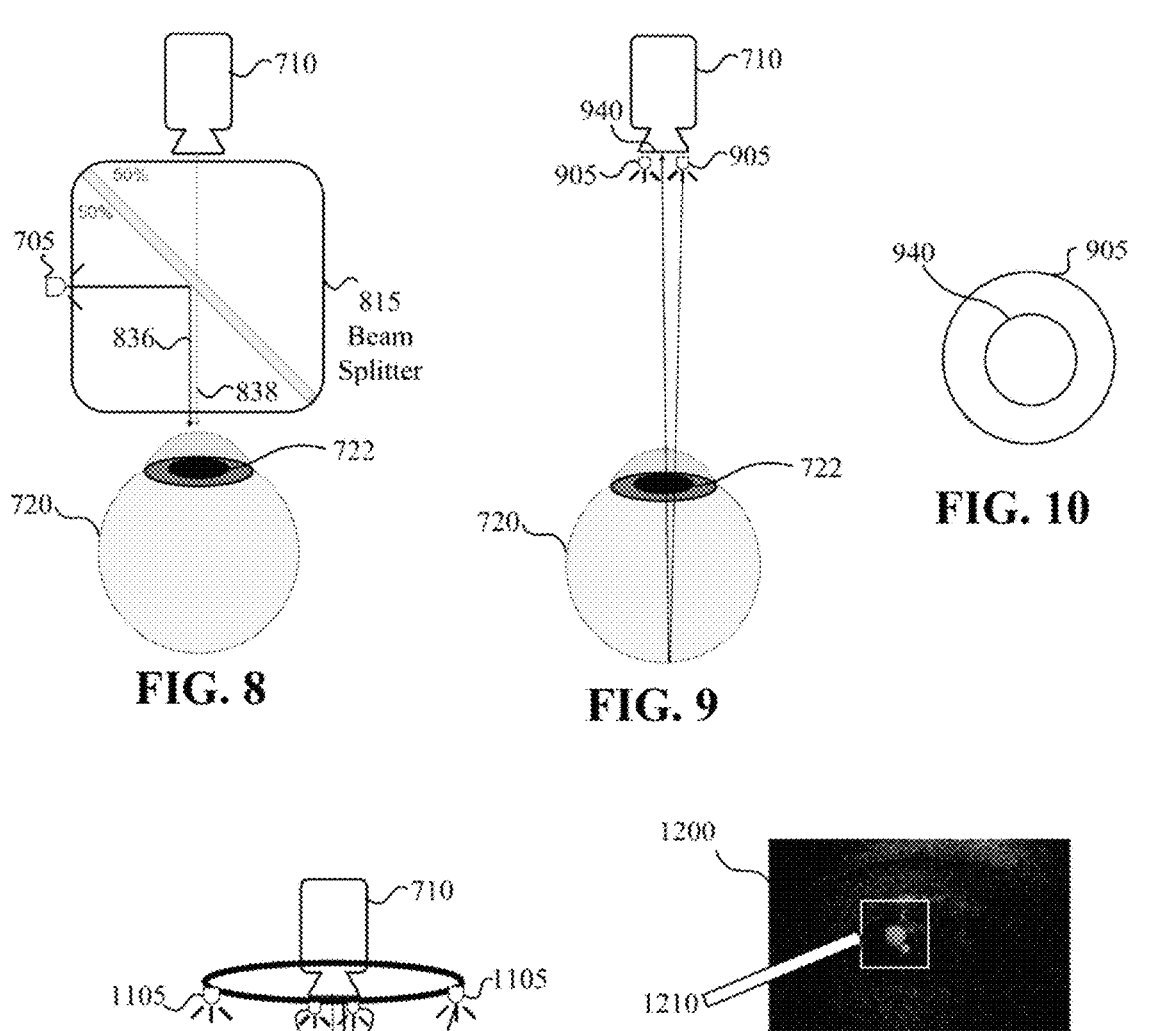
FIG. 8
FIG. 9
FIG. 10
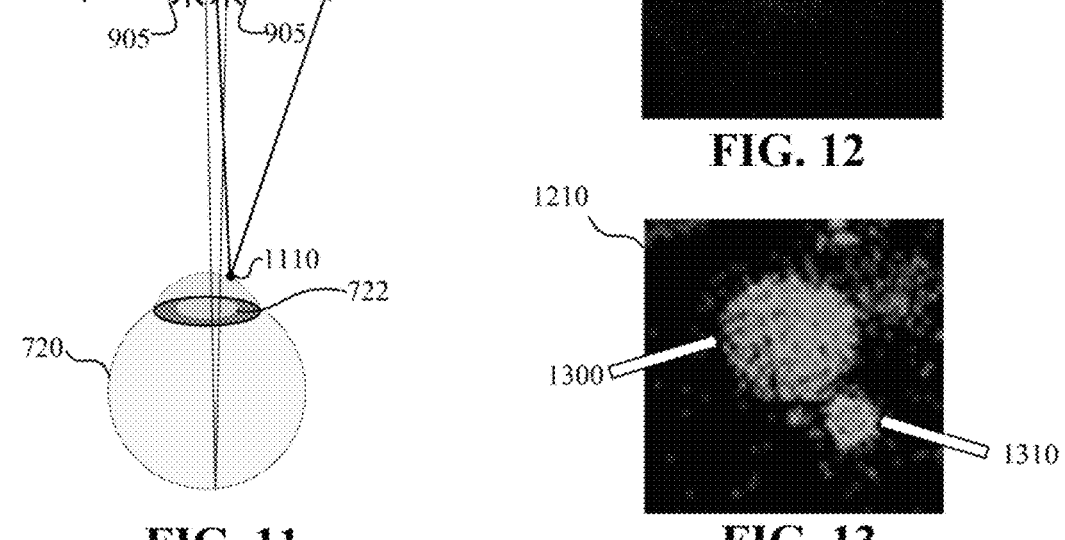
FIG. 11
FIG. 12
FIG. 13

PUPIL ASSESSMENT USING MODULATED ON-AXIS ILLUMINATION

TECHNICAL FIELD

The present disclosure generally relates to assessing characteristics of pupils of eyes, and in particular, to systems, methods, and devices for assessing pupil characteristics using light reflected off the eyes.

BACKGROUND

Some existing systems use light reflected off of the surface of the eye to estimate eye characteristics. For example, such techniques may estimate the user's gaze direction using multiple glints to identify the user's eye shape, position, and orientation. Existing pupil detection techniques may use an image sensor and integrate light intensity level over an exposure period to produce greyscale images and then attempt to detect the pupil using the greyscale images. The pupil is detected based on greyscale contrast between the pupil region and the surrounding iris region and thus rely on there being significant contrast between the pupil and the iris. Such pupil detection techniques may not be as accurate or efficient especially in circumstances in which the contrast between pupil and iris is less significant.

SUMMARY

Various implementations determine a pupil characteristic (e.g., perimeter location, pupil shape, pupil diameter, pupil center, etc.) using on-axis illumination. On-axis illumination involves producing light from a light source that is approximately on-axis with an image sensor configured to capture reflections of the light from the light source off the eye. The light from the light source may pass through the pupil into the eye and reflect off the retina to produce a bright pupil-type light pattern in data obtained by the image sensor. The light may be modulated or otherwise pulsed at a frequency and frequency segmentation may be used to distinguish reflections through the pupil off the retina from reflections of light from other light sources. In some implementations, the image sensor is an event camera that detects events. The pupil characteristics may be assessed by assessing events that recur in a given area at the given frequency. The pupil characteristics may be used to determine gaze direction or for other purposes.

Some implementations involve a method of determining pupil characteristics at an electronic device having a processor. For example, the processor may execute instructions stored in a non-transitory computer-readable medium to determine pupil characteristics based on the reflections of pulsed light off the retina and through the pupil of an eye. The method involves producing pulsed light at a frequency via a light source. The light source may be aligned approximately "on axis" with the optical axis of an image sensor. In some implementations, "approximately" on-axis illumination is achieved using a waveguide or beam-splitter. In some implementations, "approximately" on-axis illumination is achieved using a light source that is sufficiently close to the image sensor optics such that, in the intended use cases (e.g., for the intended distances of the light/source and image sensor from the eye), the axes are sufficiently aligned for light from the light source to reflect off the retina of the eye and be sensed by the image sensor. In one example, the light source is a positioned in a ring-shaped configuration around (and sufficiently close to) a lens/optic of the image sensor. In general the bright pupil effect can be observed, dependent on pupil dilation, up to an angle of about 15 degrees between the light source and the axis of the camera.

The method receives sensor data at a sensor and identifies a subset of the sensor data corresponding to reflections of the pulsed light off the retina and through a pupil of the eye based on the frequency. In some implementations, the method distinguishes data corresponding to reflections of the pulsed light from reflections of light from another light source based on the frequency. In some implementation, the image sensor is an event camera and the method determines the amount of time between events corresponding to raising or falling edges of the light reflected back through the pupil to determine events that occur at the frequency. In some implementations, the image sensor is a frame-based camera and the method subtracts one image from the next image along a sequence of images to identify light pulses that occur at the frequency in the images.

The method determines a pupil characteristic (e.g., perimeter location, pupil contour, pupil shape, pupil center, etc.) based on the subset of the sensor data corresponding to the reflections of the pulsed light off the retina and through the pupil of the eye. For example, the locations of multiple events corresponding to the pupil location may provide information about the location, shape, center, size, and orientation of the pupil. The pupil characteristic may be used to determine gaze direction or for other purposes.

Some implementations provide a device that is configured to approximately align a light source and image sensor to use frequency segmentation to determine pupil characteristics. Such a device may include a light source configured to produce pulsed light, a sensor configured to provide sensor data and having an optical axis, wherein the light source is aligned approximately on axis with the optical axis of the sensor, a processor, and a computer-readable storage medium. The computer readable medium may include instructions that upon execution by the processor cause the system to perform frequency segmentation on the sensor data to distinguish data corresponding to reflections of the pulsed light from data corresponding to reflections of light from another light source and determine a pupil characteristic based on the data corresponding to the reflections of the pulsed light. The light source may use a waveguide or beam-splitter configured to align the light of light source with the optical axis of the sensor. In another example, the light source may include a light source ring around optics of the sensor.

In accordance with some implementations, a device includes one or more processors, a non-transitory memory, and one or more programs; the one or more programs are stored in the non-transitory memory and configured to be executed by the one or more processors and the one or more programs include instructions for performing or causing performance of any of the methods described herein. In accordance with some implementations, a non-transitory computer readable storage medium has stored therein instructions, which, when executed by one or more processors of a device, cause the device to perform or cause performance of any of the methods described herein. In accordance with some implementations, a device includes: one or more processors, a non-transitory memory, and means for performing or causing performance of any of the methods described herein.

BRIEF DESCRIPTION OF THE DRAWINGS

So that the present disclosure can be understood by those of ordinary skill in the art, a more detailed description may be had by reference to aspects of some illustrative implementations, some of which are shown in the accompanying drawings.

FIG. 6 is a flowchart representation of a method of assessing pupil characteristics in accordance with some implementations.

FIG. 7 illustrates a functional block diagram illustrating differences between a bright pupil effect and a dark pupil effect according to some implementations.

FIG. 8 illustrates a functional block diagram illustrating use of a beam splitter to provide approximately on-axis illumination according to some implementations.

FIG. 9 illustrates a functional block diagram illustrating use of light source ring near the optics of a light sensor to provide approximately on-axis illumination according to some implementations.

FIG. 10 illustrates a functional block diagram illustrating the light source ring of FIG. 9.

FIG. 11 illustrates a functional block diagram illustrating combining pupil detection based on on-axis illumination with eye characteristic detection based on off-axis illumination according to certain implementations.

FIG. 12 illustrates a collection of event camera data obtained during on-axis illumination according to certain implementations.

FIG. 13 illustrates a close up view a portion of the event camera data of FIG. 12.

Figure 1:
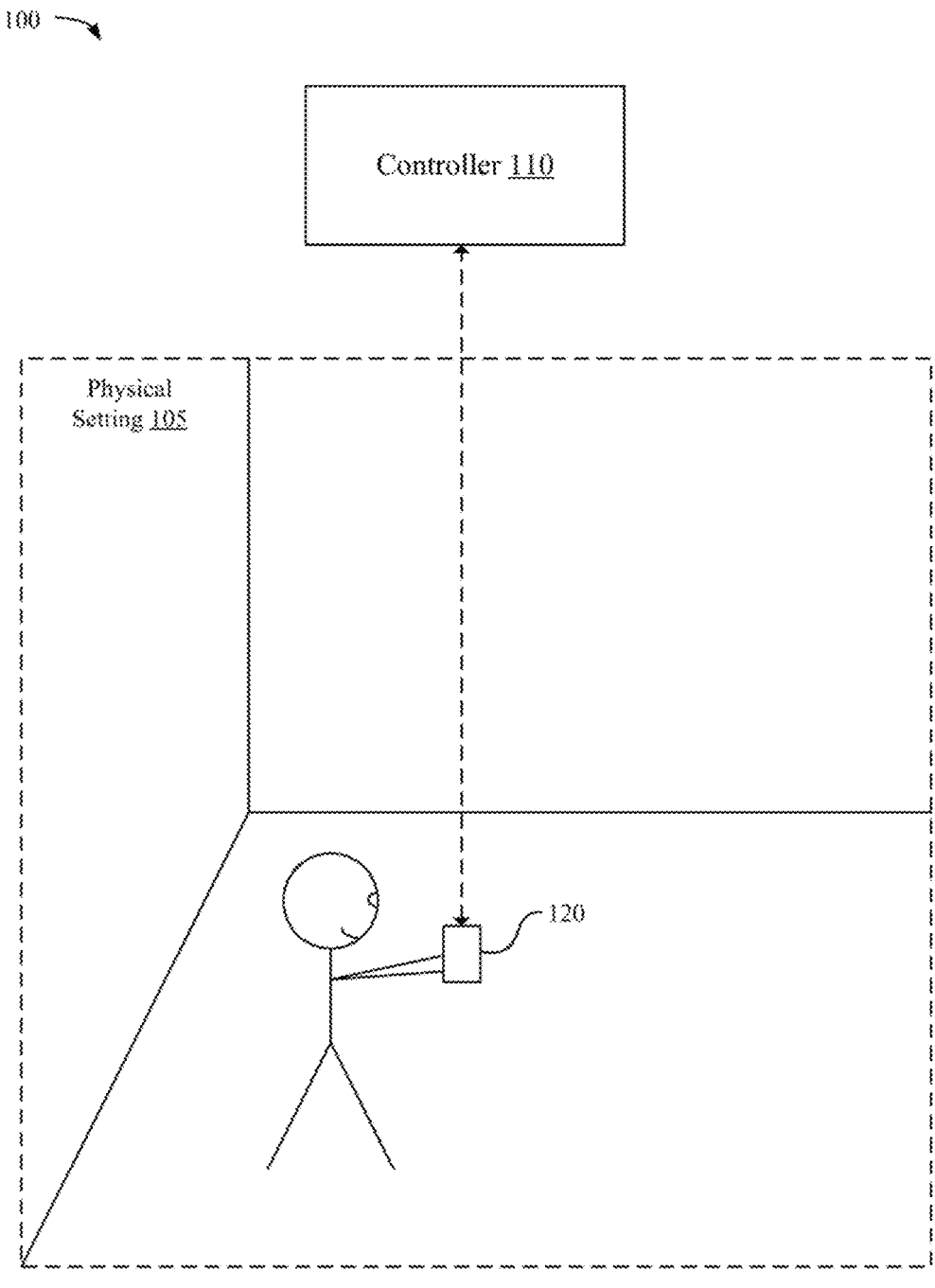
FIG. 1 is a block diagram of an example operating environment in accordance with some implementations.

In accordance with common practice the various features illustrated in the drawings may not be drawn to scale. Accordingly, the dimensions of the various features may be arbitrarily expanded or reduced for clarity. In addition, some of the drawings may not depict all of the components of a given system, method or device. Finally, like reference numerals may be used to denote like features throughout the specification and figures.

DESCRIPTION

Numerous details are described in order to provide a thorough understanding of the example implementations shown in the drawings. However, the drawings merely show some example aspects of the present disclosure and are therefore not to be considered limiting. Those of ordinary skill in the art will appreciate that other effective aspects and/or variants do not include all of the specific details described herein. Moreover, well-known systems, methods, components, devices and circuits have not been described in exhaustive detail so as not to obscure more pertinent aspects of the example implementations described herein.

A pupil characteristic assessing system includes a light source, an image sensor, and a processor that performs pupil characteristic assessments on data received from the light sensor regarding light from the light source reflected off an eye of a user. In various implementations, a pupil characteristic is determined using on-axis illumination from the light source so that light from the light source is reflected off the retina of the eye to produce a bright pupil-type light pattern in data obtained by the image sensor. The light may be modulated or otherwise pulsed at a frequency and frequency segmentation may be used to distinguish reflections through the pupil off the retina from reflections of light from other light sources. In some implementations, the image sensor is a frame-based camera and the method subtracts one image from the next image along a sequence of images to identify light pulses that occur at the frequency in the images.

In some implementation, the image sensor is an event camera and the amount of time between events corresponding to light reflected off the retina and through the pupil is used to determine events that occur at the frequency. The event camera has light sensors at multiple respective locations. In response to a particular light sensor detecting a change in intensity of light, the light sensor generates an event message indicating a particular location of the particular light sensor. An event camera may include or be referred to as a dynamic vision sensor (DVS), a silicon retina, an event-based camera, or a frame-less camera. Thus, the event camera generates (and transmits) data regarding changes in light intensity as opposed to a larger amount of data regarding absolute intensity at each light sensor.

FIG. 1 is a block diagram of an example operating environment 100 in accordance with some implementations. While pertinent features are shown, those of ordinary skill in the art will appreciate from the present disclosure that various other features have not been illustrated for the sake of brevity and so as not to obscure more pertinent aspects of the example implementations disclosed herein. To that end, as a non-limiting example, the operating environment 100 includes a controller 110 and a device 120.

In some implementations, the controller 110 is configured to manage and coordinate an experience for the user. In some implementations, the controller 110 includes a suitable combination of software, firmware, and/or hardware. The controller 110 is described in greater detail below with respect to FIG. 2. In some implementations, the controller 110 is a computing device that is local or remote relative to the physical setting 105. In one example, the controller 110 is a local server located within the physical setting 105. In another example, the controller 110 is a remote server located outside of the physical setting 105 (e.g., a cloud server, central server, etc.). In some implementations, the controller 110 is communicatively coupled with the device 120 via one or more wired or wireless communication channels 144 (e.g., BLUETOOTH, IEEE 802.11x, IEEE 802.16x, IEEE 802.3x, etc.).

In some implementations, the device 120 is configured to present an environment to the user. In some implementations, the device 120 includes a suitable combination of software, firmware, and/or hardware. The device 120 is described in greater detail below with respect to FIG. 3. In some implementations, the functionalities of the controller 110 are provided by and/or combined with the device 120.

According to some implementations, the device 120 presents a simulated reality (SR) setting (e.g., an augmented reality/virtual reality (AR/VR) setting) to the user while the user is virtually and/or physically present within the physical setting 105. In some implementations, while presenting an experience, the device 120 is configured to present content and to enable optical see-through of the physical setting 105. In some implementations, while presenting a setting, the device 120 is configured to present VR content and to enable video pass-through of the physical setting 105.

In some implementations, the user wears the device 120 as a head mounted device (HMD) on his or her head. As such, the device 120 includes one or more displays provided to display content. For example, the device 120 encloses the field-of-view of the user. In some implementations, the device 120 is a handheld electronic device (e.g., a smartphone or a tablet) configured to present content to the user. In some implementations, the device 120 is replaced with a chamber, enclosure, or room configured to present content in which the user does not wear or hold the device 120.

Figure 2:
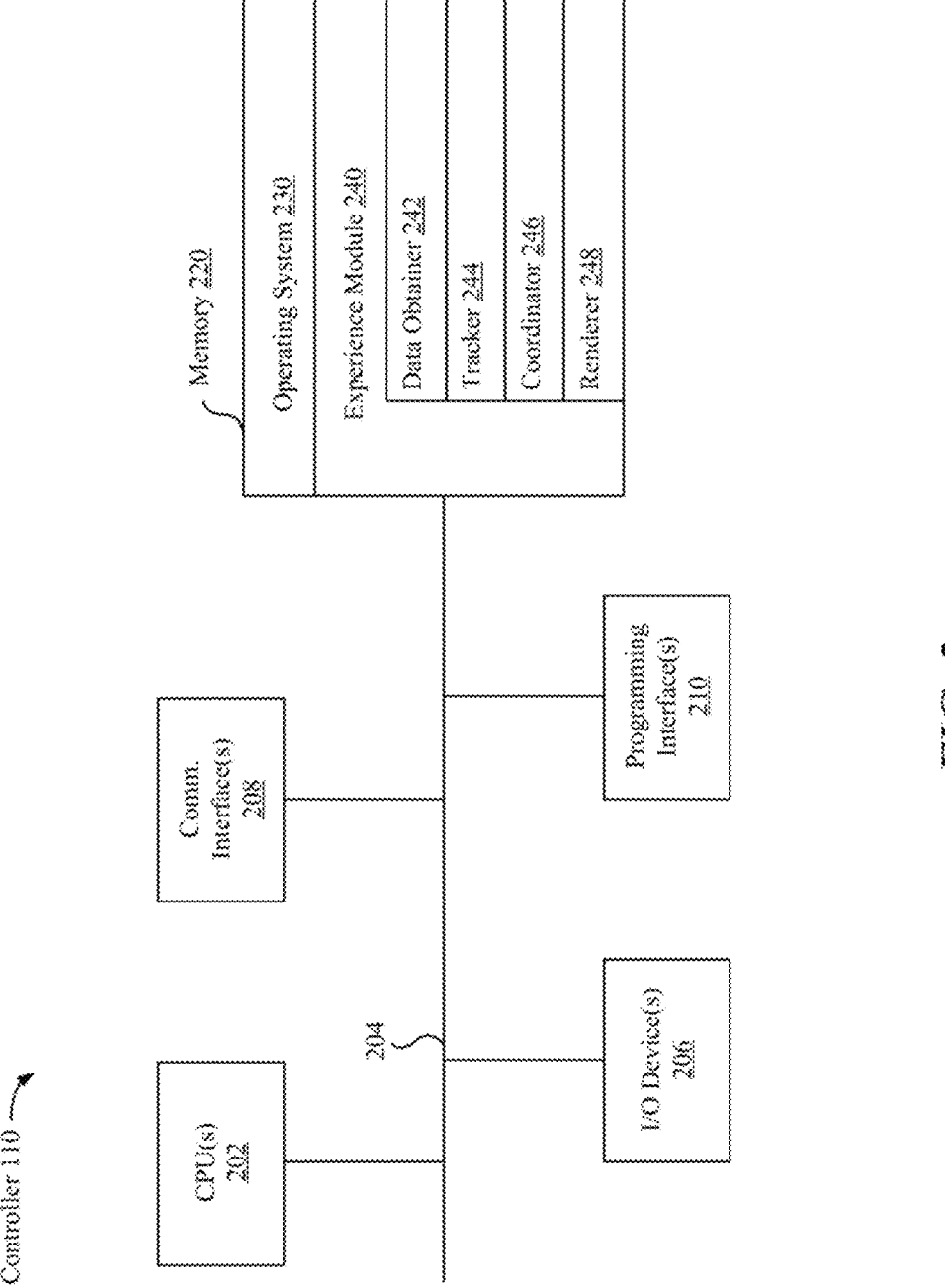
FIG. 2 is a block diagram of an example controller in accordance with some implementations.

FIG. 2 is a block diagram of an example of the controller 110 in accordance with some implementations. While certain specific features are illustrated, those skilled in the art will appreciate from the present disclosure that various other features have not been illustrated for the sake of brevity, and so as not to obscure more pertinent aspects of the implementations disclosed herein. To that end, as a non-limiting example, in some implementations the controller 110 includes one or more processing units 202 (e.g., microprocessors, application-specific integrated-circuits (ASICs), field-programmable gate arrays (FPGAs), graphics processing units (GPUs), central processing units (CPUs), processing cores, and/or the like), one or more input/output (I/O) devices 206, one or more communication interfaces 208 (e.g., universal serial bus (USB), FIREWIRE, THUNDERBOLT, IEEE 802.3x, IEEE 802.11x, IEEE 802.16x, global system for mobile communications (GSM), code division multiple access (CDMA), time division multiple access (TDMA), global positioning system (GPS), infrared (IR), BLUETOOTH, ZIGBEE, and/or the like type interface), one or more programming (e.g., I/O) interfaces 210, a memory 220, and one or more communication buses 204 for interconnecting these and various other components.

In some implementations, the one or more communication buses 204 include circuitry that interconnects and controls communications between system components. In some implementations, the one or more I/O devices 206 include at least one of a keyboard, a mouse, a touchpad, a joystick, one or more microphones, one or more speakers, one or more image sensors, one or more displays, and/or the like.

The memory 220 includes high-speed random-access memory, such as dynamic random-access memory (DRAM), static random-access memory (SRAM), double-data-rate random-access memory (DDR RANI), or other random-access solid-state memory devices. In some implementations, the memory 220 includes non-volatile memory, such as one or more magnetic disk storage devices, optical disk storage devices, flash memory devices, or other non-volatile solid-state storage devices. The memory 220 optionally includes one or more storage devices remotely located from the one or more processing units 202. The memory 220 comprises a non-transitory computer readable storage medium. In some implementations, the memory 220 or the non-transitory computer readable storage medium of the memory 220 stores the following programs, modules and data structures, or a subset thereof including an optional operating system 230 and an experience module 240.

The operating system 230 includes procedures for handling various basic system services and for performing hardware dependent tasks. In some implementations, the experience module 240 is configured to manage and coordinate one or more experiences for one or more users (e.g., a single experience for one or more users, or multiple experiences for respective groups of one or more users). To that end, in various implementations, the experience module 240 includes a data obtainer 242, a tracker 244, a coordinator 246, and a renderer 248.

In some implementations, the data obtainer 242 is configured to obtain data (e.g., presentation data, interaction data, sensor data, location data, etc.) from at least the device 120. To that end, in various implementations, the data obtainer 242 includes instructions and/or logic therefor, and heuristics and metadata therefor.

In some implementations, the tracker 244 is configured to map the physical setting 105 and to track the position/location of at least the device 120 with respect to the physical setting 105. In some implementations, the tracker 244 is configured to perform pupil assessment via one or more of the techniques disclosed herein. To that end, in various implementations, the tracker 244 includes instructions and/or logic therefor, and heuristics and metadata therefor.

In some implementations, the coordinator 246 is configured to manage and coordinate the experience presented to the user by the device 120. To that end, in various implementations, the coordinator 246 includes instructions and/or logic therefor, and heuristics and metadata therefor.

In some implementations, the renderer 248 is configured to render content for display on the device 120. To that end, in various implementations, the renderer 248 includes instructions and/or logic therefor, and heuristics and metadata therefor.

Although the data obtainer 242, the tracker 244, the coordinator 246, and the renderer 248 are shown as residing on a single device (e.g., the controller 110), it should be understood that in other implementations, any combination of these elements may be located in separate computing devices.

Moreover, FIG. 2 is intended more as functional description of the various features which are present in a particular implementation as opposed to a structural schematic of the implementations described herein. As recognized by those of ordinary skill in the art, items shown separately could be combined and some items could be separated. For example, some functional modules shown separately in FIG. 2 could be implemented in a single module and the various functions of single functional blocks could be implemented by one or more functional blocks in various implementations. The actual number of modules and the division of particular functions and how features are allocated among them will vary from one implementation to another and, in some implementations, depends in part on the particular combination of hardware, software, and/or firmware chosen for a particular implementation.

Figure 3:
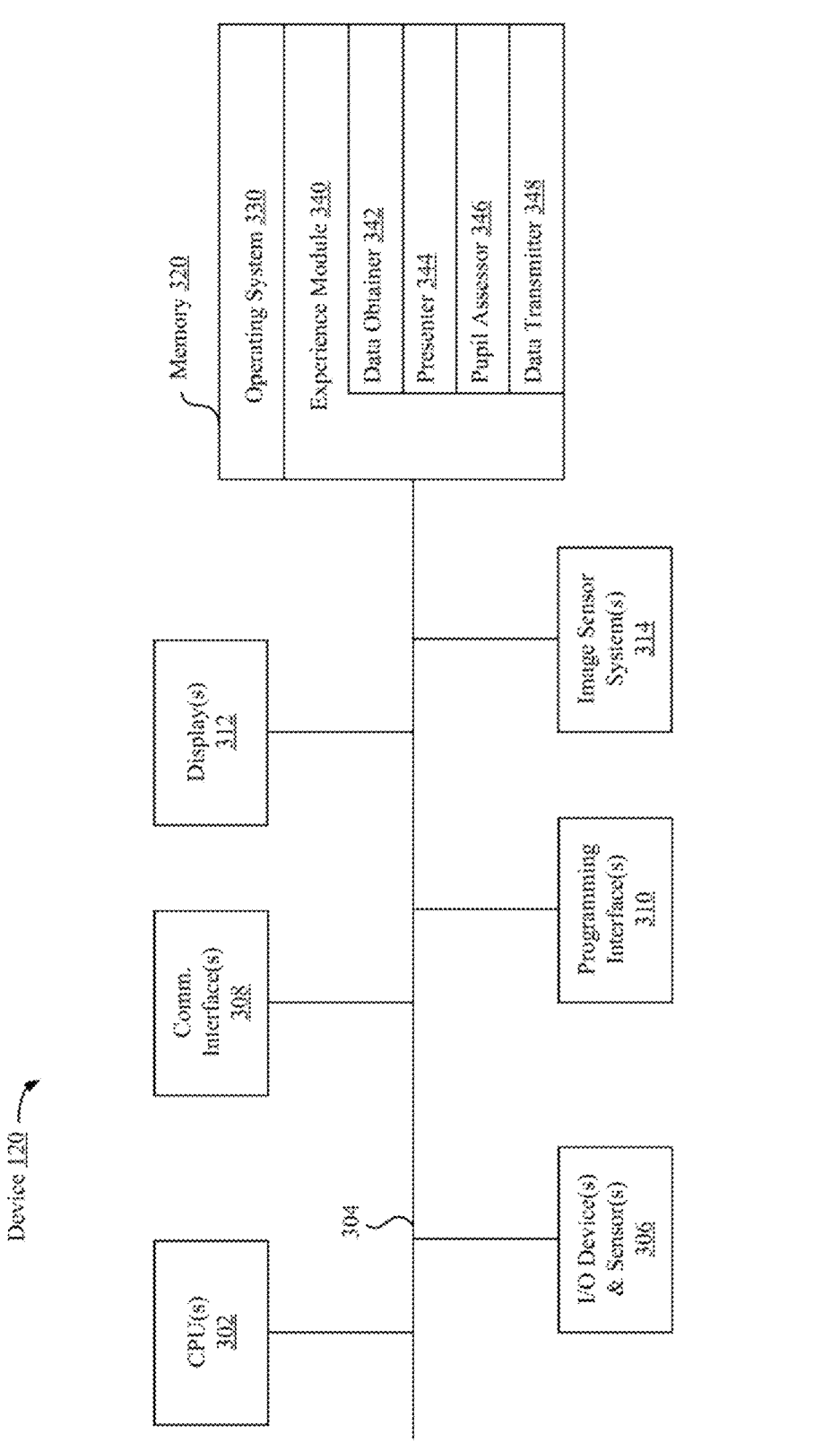
FIG. 3 is a block diagram of an example device in accordance with some implementations.

FIG. 3 is a block diagram of an example of the device 120 in accordance with some implementations. While certain specific features are illustrated, those skilled in the art will appreciate from the present disclosure that various other features have not been illustrated for the sake of brevity, and so as not to obscure more pertinent aspects of the implementations disclosed herein. To that end, as a non-limiting example, in some implementations the device 120 includes one or more processing units 302 (e.g., microprocessors, ASICs, FPGAs, GPUs, CPUs, processing cores, and/or the like), one or more input/output (I/O) devices and sensors 306, one or more communication interfaces 308 (e.g., USB, FIREWIRE, THUNDERBOLT, IEEE 802.3x, IEEE 802.11x, IEEE 802.16x, GSM, CDMA, TDMA, GPS, IR, BLUETOOTH, ZIGBEE, SPI, I2C, and/or the like type interface), one or more programming (e.g., I/O) interfaces 310, one or more displays 312, one or more interior and/or exterior facing image sensor systems 314, a memory 320, and one or more communication buses 304 for interconnecting these and various other components.

In some implementations, the one or more communication buses 304 include circuitry that interconnects and controls communications between system components. In some implementations, the one or more I/O devices and sensors 306 include at least one of an inertial measurement unit (IMU), an accelerometer, a magnetometer, a gyroscope, a thermometer, one or more physiological sensors (e.g., blood pressure monitor, heart rate monitor, blood oxygen sensor, blood glucose sensor, etc.), one or more microphones, one or more speakers, a haptics engine, one or more depth sensors (e.g., a structured light, a time-of-flight, or the like), and/or the like.

In some implementations, the one or more displays 312 are configured to present the experience to the user. In some implementations, the one or more displays 312 correspond to holographic, digital light processing (DLP), liquid-crystal display (LCD), liquid-crystal on silicon (LCoS), organic light-emitting field-effect transitory (OLET), organic light-emitting diode (OLED), surface-conduction electron-emitter display (SED), field-emission display (FED), quantum-dot light-emitting diode (QD-LED), micro-electromechanical system (MEMS), and/or the like display types. In some implementations, the one or more displays 312 correspond to diffractive, reflective, polarized, holographic, etc. waveguide displays. For example, the device 120 includes a single display. In another example, the device 120 includes an display for each eye of the user. In some implementations, the one or more displays 312 are capable of presenting SR content.

In some implementations, the one or more image sensor systems 314 are configured to obtain image data that corresponds to at least a portion of the face of the user that includes the eyes of the user. For example, the one or more image sensor systems 314 include one or more RGB cameras (e.g., with a complimentary metal-oxide-semiconductor (CMOS) image sensor or a charge-coupled device (CCD) image sensor), monochrome cameras, IR cameras, event-based cameras, and/or the like. In various implementations, the one or more image sensor systems 314 further include illumination sources that emit light upon the portion of the face of the user, such as a flash, a glint source, or on-axis illumination. In some implementations, an image sensor is configured to be approximately on-axis with an optical axis of a light source.

The memory 320 includes high-speed random-access memory, such as DRAM, SRAM, DDR RAM, or other random-access solid-state memory devices. In some implementations, the memory 320 includes non-volatile memory, such as one or more magnetic disk storage devices, optical disk storage devices, flash memory devices, or other non-volatile solid-state storage devices. The memory 320 optionally includes one or more storage devices remotely located from the one or more processing units 302. The memory 320 comprises a non-transitory computer readable storage medium. In some implementations, the memory 320 or the non-transitory computer readable storage medium of the memory 320 stores the following programs, modules and data structures, or a subset thereof including an optional operating system 330 and an experience module 340.

The operating system 330 includes procedures for handling various basic system services and for performing hardware dependent tasks. In some implementations, the experience module 340 is configured to present content to the user via the one or more displays 312. To that end, in various implementations, the presentation module 340 includes a data obtainer 342, a presenter 344, a pupil assessor 346, and a data transmitter 348.

In some implementations, the data obtainer 342 is configured to obtain data (e.g., presentation data, interaction data, sensor data, location data, etc.) from at least the controller 110 and/or the I/O devices and sensor(s) 306. To that end, in various implementations, the data obtainer 342 includes instructions and/or logic therefor, and heuristics and metadata therefor.

In some implementations, the presenter 344 is configured to present content via the one or more displays 312. To that end, in various implementations, the presenting unit 344 includes instructions and/or logic therefor, and heuristics and metadata therefor.

In some implementations, the pupil assessor 346 is configured to assess pupil characteristics via one or more of the techniques disclosed herein. To that end, in various implementations, the pupil assessor 346 includes instructions and/or logic therefor, configured neural networks, and heuristics and metadata therefor.

In some implementations, the data transmitter 348 is configured to transmit data (e.g., presentation data, location data, etc.) to at least the controller 110. To that end, in various implementations, the data transmitter 348 includes instructions and/or logic therefor, and heuristics and metadata therefor.

Although these elements are shown as residing on a single device (e.g., the device 120), it should be understood that in other implementations, any combination of the elements may be located in separate computing devices. Moreover, FIG. 3 is intended more as functional description of the various features which are present in a particular implementation as opposed to a structural schematic of the implementations described herein. As recognized by those of ordinary skill in the art, items shown separately could be combined and some items could be separated. For example, some functional modules shown separately in FIG. 3 could be implemented in a single module and the various functions of single functional blocks could be implemented by one or more functional blocks in various implementations. The actual number of modules and the division of particular functions and how features are allocated among them will vary from one implementation to another and, in some implementations, depends in part on the particular combination of hardware, software, and/or firmware chosen for a particular implementation.

Figure 4:
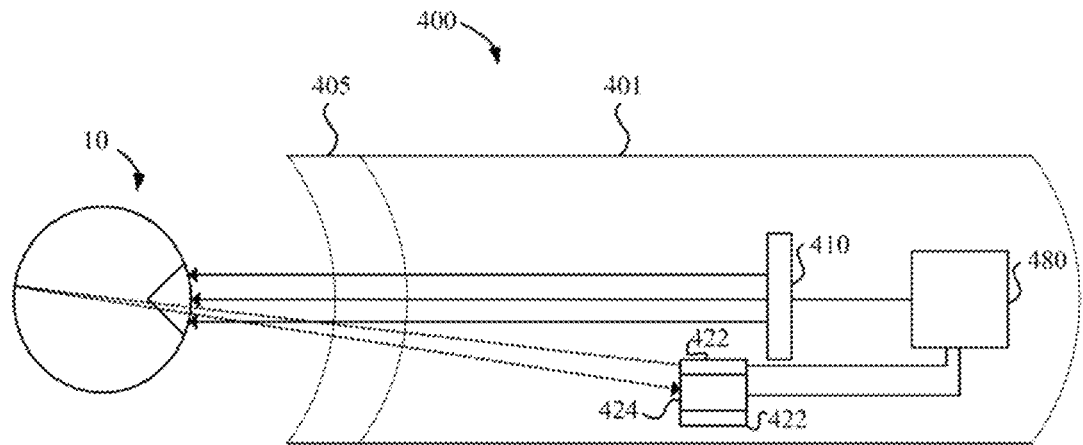
FIG. 4 is a block diagram of an example head-mounted device (HMD) in accordance with some implementations.

FIG. 4 illustrates a block diagram of a head-mounted device 400 in accordance with some implementations. The head-mounted device 400 includes a housing 401 (or enclosure) that houses various components of the head-mounted device 400. The housing 401 includes (or is coupled to) an eye pad 405 disposed at a proximal (to the user 10) end of the housing 401. In various implementations, the eye pad 405 is a plastic or rubber piece that comfortably and snugly keeps the head-mounted device 400 in the proper position on the face of the user 10 (e.g., surrounding the eye of the user 10).

The housing 401 houses a display 410 that displays an image, emitting light towards onto the eye of a user 10. In various implementations, the display 410 emits the light through an eyepiece (not shown) that refracts the light emitted by the display 410, making the display appear to the user 10 to be at a virtual distance farther than the actual distance from the eye to the display 410. For the user to be able to focus on the display 410, in various implementations, the virtual distance is at least greater than a minimum focal distance of the eye (e.g., 7 cm). Further, in order to provide a better user experience, in various implementations, the virtual distance is greater than 1 meter.

Although FIG. 4 illustrates a head-mounted device 400 including a display 410 and an eye pad 405, in various implementations, the head-mounted device 400 does not include a display 410 or includes an optical see-through display without including an eye pad 405.

The housing 401 also houses a pupil assessment system including one or more light sources 422, image sensor 424, and a controller 480. The one or more light sources 422 emit light towards the eye of the user 10 that reflects light (e.g., a directional beam) that can be detected by the sensor 424. Based on the reflections, the controller 480 can determine pupil characteristics of the user 10. As another example, the controller 480 can determine a pupil center, a pupil size, gaze direction, or a point of regard. Thus, in various implementations, the light is emitted by the one or more light sources 422, reflects off the eye of the user 10, and is detected by the sensor 424. In various implementations, the light from the eye of the user 10 is reflected off a hot mirror or passed through an eyepiece before reaching the sensor 424.

The display 410 may emit light in a first wavelength range and the one or more light sources 422 may emit light in a second wavelength range. Similarly, the sensor 424 may detects light in the second wavelength range. In various implementations, the first wavelength range is a visible wavelength range (e.g., a wavelength range within the visible spectrum of approximately 400-700 nm) and the second wavelength range is a near-infrared wavelength range (e.g., a wavelength range within the near-infrared spectrum of approximately 700-1400 nm).

In various implementations, the one or more light sources 422 modulate or otherwise pulse the emitted light. For example, in various implementations, a light source of the one or more light sources 422 is modulated at a frequency (e.g., 600 Hz). In various implementations, the one or more light sources 422 modulate the emitted light according to an orthogonal code, such as those which may be used in CDMA (code-divisional multiplex access) communications. For example, the rows or columns of a Walsh matrix can be used as the orthogonal codes.

In various implementations, the one or more light sources 422 modulate the emitted light between a high intensity value and a low intensity value. Thus, at various times, the intensity of the light emitted by the light source is either the high intensity value or the low intensity value. In various implementation, the low intensity value is zero. Thus, in various implementations, the one or more light sources 422 modulate the intensity of emitted light between an on state (at the high intensity value) and an off state (at the low intensity value).

In various implementations, the one or more light sources 422 modulate the emitted light according to user biometrics. For example, if the user is blinking more than normal, has an elevated heart rate, or is registered as a child, the one or more light sources 422 decreases the emitted light (or the total of all light emitted by the light sources) to reduce stress upon the eye. As another example, the one or more light sources 422 modulate the emitted light based on an eye color of the user, as spectral reflectivity may differ for blue eyes as compared to brown eyes.

In various implementations, the one or more light sources 422 modulate the emitted light according to a presented user interface (e.g., what is displayed on the display 410). For example, if the display 410 is unusually bright (e.g., a video of an explosion is being displayed), the one or more light sources 422 increase the intensity of the emitted light to compensate for potential interference from the display 410.

In various implementations, the one or more other light sources (not shown) emit light towards the eye of the user which reflects in the form of one or more glints off the surface of the eye.

In various implementations, the sensor 424 is a frame/shutter-based camera that, at a particular point in time or multiple points in time at a frame rate, generates an image of the eye of the user 10. Each image includes a matrix of pixel values corresponding to pixels of the image which correspond to locations of a matrix of light sensors of the camera.

In various implementations, the camera 424 is an event camera comprising a plurality of light sensors (e.g., a matrix of light sensors) at a plurality of respective locations that, in response to a particular light sensor detecting a change in intensity of light, generates an event message indicating a particular location of the particular light sensor.

In various implementations, pupil characteristic assessment is used to facilitate gaze tracking, which may be used to enable user interaction (e.g., the user 10 selects an option on the display 410 by looking at it), provide foveated rendering (e.g., present a higher resolution in an area of the display 410 the user 10 is looking at and a lower resolution elsewhere on the display 410), or reduce geometric distortion (e.g., in 3D rendering of objects on the display 410).

Figure 5:
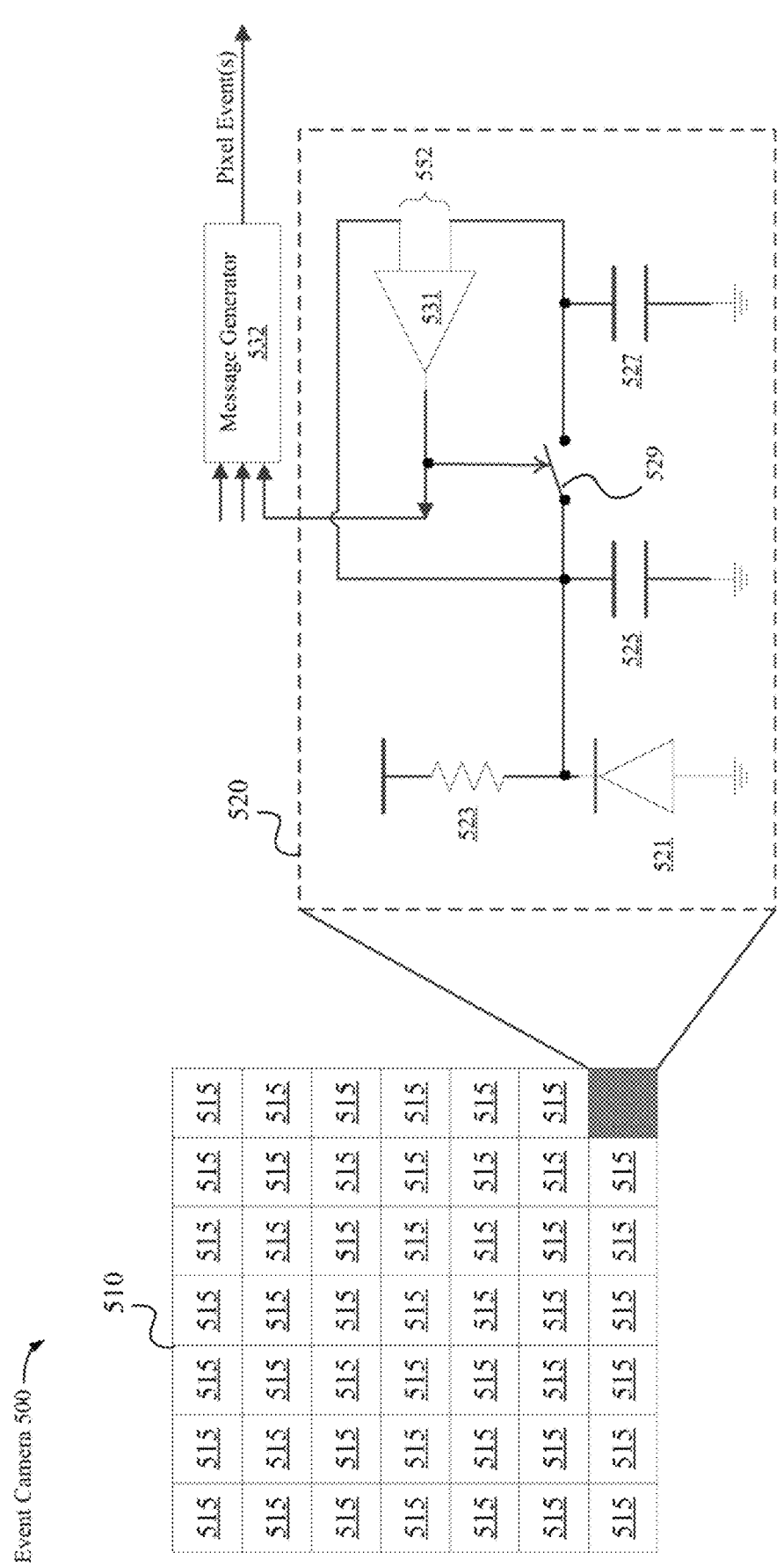
FIG. 5 illustrates a block diagram of an event camera in accordance with some implementations.

FIG. 5 illustrates a functional block diagram of an event camera 500 in accordance with some implementations. The event camera 500 includes a plurality of light sensors 515 respectively coupled to a message generator 532. In various implementations, the plurality of light sensors 515 are arranged in a matrix 510 of rows and columns and, thus, each of the plurality of light sensors 515 is associated with a row value and a column value.

Each of the plurality of light sensors 515 includes a light sensor 520 illustrated in detail in FIG. 5. The light sensor 520 includes a photodiode 521 in series with a resistor 523 between a source voltage and a ground voltage. The voltage across the photodiode 521 is proportional to the intensity of light impinging on the light sensor 520. The light sensor 520 includes a first capacitor 525 in parallel with the photodiode 521. Accordingly, the voltage across the first capacitor 525 is the same as the voltage across the photodiode 521 (e.g., proportional to the intensity of light detected by the light sensor 520).

The light sensor 520 includes a switch 529 coupled between the first capacitor 525 and a second capacitor 527. The second capacitor 527 is coupled between the switch and the ground voltage. Accordingly, when the switch 529 is closed, the voltage across the second capacitor 527 is the same as the voltage across the first capacitor 525 (e.g., proportional to the intensity of light detected by the light sensor 520). When the switch 529 is open, the voltage across the second capacitor 527 is fixed at the voltage across the second capacitor 527 when the switch 529 was last closed.

The voltage across the first capacitor 525 and the voltage across the second capacitor 527 are fed to a comparator 531. When the difference 552 between the voltage across the first capacitor 525 and the voltage across the second capacitor 527 is less than a threshold amount, the comparator 531 outputs a '0' voltage. When the voltage across the first capacitor 525 is higher than the voltage across the second capacitor 527 by at least the threshold amount, the comparator 531 outputs a '1' voltage. When the voltage across the first capacitor 525 is less than the voltage across the second capacitor 527 by at least the threshold amount, the comparator 531 outputs a '−1' voltage.

When the comparator 531 outputs a '1' voltage or a '−1' voltage, the switch 529 is closed and the message generator 532 receives this digital signal and generates a pixel event message.

As an example, at a first time, the intensity of light impinging on the light sensor 520 is a first light value. Accordingly, the voltage across the photodiode 521 is a first voltage value. Likewise, the voltage across the first capacitor 525 is the first voltage value. For this example, the voltage across the second capacitor 527 is also the first voltage value. Accordingly, the comparator 531 outputs a '0' voltage, the switch 529 remains closed, and the message generator 532 does nothing.

At a second time, the intensity of light impinging on the light sensor 520 increases to a second light value. Accordingly, the voltage across the photodiode 521 is a second voltage value (higher than the first voltage value). Likewise, the voltage across the first capacitor 525 is the second voltage value. Because the switch 529 is open, the voltage across the second capacitor 527 is still the first voltage value. Assuming that the second voltage value is at least the threshold value greater than the first voltage value, the comparator 531 outputs a '1' voltage, closing the switch 529, and the message generator 532 generates an event message based on the received digital signal.

With the switch 529 closed by the '1' voltage from the comparator 531, the voltage across the second capacitor 527 is changed from the first voltage value to the second voltage value. Thus, the comparator 531 outputs a '0' voltage, opening the switch 529.

At a third time, the intensity of light impinging on the light sensor 520 increases (again) to a third light value. Accordingly, the voltage across the photodiode 521 is a third voltage value (higher than the second voltage value). Likewise, the voltage across the first capacitor 525 is the third voltage value. Because the switch 529 is open, the voltage across the second capacitor 527 is still the second voltage value. Assuming that the third voltage value is at least the threshold value greater than the second voltage value, the comparator 531 outputs a '1' voltage, closing the switch 529, and the message generator 532 generates an event message based on the received digital signal.

With the switch 529 closed by the '1' voltage from the comparator 531, the voltage across the second capacitor 527 is changed from the second voltage value to the third voltage value. Thus, the comparator 531 outputs a '0' voltage, opening the switch 529.

At a fourth time, the intensity of light impinging on the light sensor 520 decreases back to second light value. Accordingly, the voltage across the photodiode 521 is the second voltage value (less than the third voltage value). Likewise, the voltage across the first capacitor 525 is the second voltage value. Because the switch 529 is open, the voltage across the second capacitor 527 is still the third voltage value. Thus, the comparator 531 outputs a '−1' voltage, closing the switch 529, and the message generator 532 generates an event message based on the received digital signal.

With the switch 529 closed by the '−1' voltage from the comparator 531, the voltage across the second capacitor 527 is changed from the third voltage value to the second voltage value. Thus, the comparator 531 outputs a '0' voltage, opening the switch 529.

The message generator 532 receives, at various times, digital signals from each of the plurality of light sensors 510 indicating an increase in the intensity of light ('1' voltage) or a decrease in the intensity of light ('−1' voltage). In response to receiving a digital signal from a particular light sensor of the plurality of light sensors 510, the message generator 532 generates a pixel event message.

In various implementations, each pixel event message indicates, in a location field, the particular location of the particular light sensor. In various implementations, the event message indicates the particular location with a pixel coordinate, such as a row value (e.g., in a row field) and a column value (e.g., in a column field). In various implementations, the event message further indicates, in a polarity field, the polarity of the change in intensity of light. For example, the event message may include a '1' in the polarity field to indicate an increase in the intensity of light and a '0' in the polarity field to indicate a decrease in the intensity of light. In various implementations, the event message further indicates, in a time field, a time the change in intensity in light was detected (e.g., a time the digital signal was received). In various implementations, the event message indicates, in an absolute intensity field (not shown), as an alternative to or in addition to the polarity, a value indicative of the intensity of detected light.

FIG. 6 is a flowchart representation of a method 600 of assessing pupil characteristics in accordance with some implementations. In some implementations, the method 600 is performed by a device (e.g., controller 110 of FIGS. 1 and 2), such as a mobile device, desktop, laptop, or server device. The method 600 can be performed on a device (e.g., device 120 of FIGS. 1 and 3) that has a screen for displaying 2D images and/or a screen for viewing stereoscopic images such as a head-mounted display (HMD). In some implementations, the method 600 is performed by processing logic, including hardware, firmware, software, or a combination thereof. In some implementations, the method 600 is performed by a processor executing code stored in a non-transitory computer-readable medium (e.g., a memory).

At block 610, the method 600 produces pulsed light at a frequency via a light source. The frequency may be greater than a frequency of motion of physical objects in a physical environment of the eye. The frequency may be greater than the frequency of motion in content being viewed by the user. The light, in some implementations, is infrared (IR) light. In some implementations, the light is pulsed using a light source that is aligned approximately "on axis" with the axis of the light sensor. In some implementations, the approximately on-axis illumination is produced via a waveguide or beam-splitter. In some implementations, the approximately on-axis illumination is produced via a light source sufficiently near the optics of the sensor. In some implementations, the approximately on-axis illumination is produced via a light source ring around optics of the sensor.

At block 620, the method 600 receives sensor data at a sensor. In some implementations, the sensor is an event camera. In some implementations, the sensor is a frame-based camera capable of capturing frames at sufficient frequency to identify a frequency of pulsing of the pulsed light (e.g., 1000 fps).

At block 630, the method 600 identifies a subset of the sensor data corresponding to reflections of the pulsed light off a retina and through a pupil of an eye based on the frequency. In some implementations, this involves distinguishing sensor data corresponding to reflections of the pulsed light from reflections of light from another light source based on the frequency. The sensor may be an event camera or a frame-based camera.

In implementations in which the sensor is an event camera, the subset of the sensor data corresponding to reflections of the pulsed light may be identified by determining amounts of time between events and determining whether the events correspond to reflections of the pulsed light based on the amounts of time and the frequency. Using an event camera may provide advantages over techniques that rely solely on shutter-based (e.g., frame-based) camera data. Event cameras may efficiently capture data at a very high sample rate and thus be well suited for efficiently and accurately identifying that reflected light is being pulsed at a particular frequency.

In implementations in which the sensor is a frame-based camera that captures images, the subset of the sensor data corresponding to reflections of the pulsed light may be identified by subtracting the images from one another to identify light pulses at the frequency.

At block 640, the method 600 involves determining a pupil characteristic (e.g., perimeter location, pupil shape, pupil center, etc.) based on the subset of the sensor data corresponding to the reflections of the pulsed light off the retina and through the pupil of the eye.

In various implementations, the pupil characteristic assessment of FIG. 6 is used to facilitate gaze tracking. For example, a pupil center may be determined based on the pupil characteristic assessment and used as part of a gaze direction determination that determines gaze direction based on pupil center, cornea center, eyeball center, etc. In some implementations, a gaze direction is determined based on an ellipse corresponding to a shape of a pupil. In some implementations, additional information about the eye is used to determine the gaze direction. For example, an additional light source may be used to produce glints off the cornea of the eye to provide information about the location and orientation of the cornea or other eye characteristics. Accordingly, in some implementations gaze direction is determined based on a pupil assessment and based on one or more glints of light reflected from a second light source off a cornea surface of the eye.

Gaze direction can be used for numerous purposes. In one example, the gaze direction that is determined or updated is used to identify an item displayed on a display, e.g., to identify what button, image, text, or other user interface item a user is looking at. In another example, the gaze characteristic that is determined or updated is used to display a movement of a graphical indicator (e.g., a cursor or other user controlled icon) on a display. In another example, the gaze characteristic that is determined or updated is used to select an item (e.g., via a cursor selection command) displayed on a display. For example, a particular gaze movement pattern can be recognized and interpreted as a particular command.

In some implementations, the gaze tracking is performed on two eyes of a same individual concurrently. In implementations in which images of both eyes are captured or derived, the system may determine or produce output useful in determining a convergence point of gaze directions from the two eyes. The system could additionally or alternatively be configured to account for extraordinary circumstances such as optical axes that do not align.

In some implementations, post-processing of gaze direction is employed. Noise in the tracked gaze direction can be reduced using filtering and prediction methods, for example, using a Kalman filter. These methods can also be used for interpolation/extrapolation of the gaze direction over time. For example, the methods can be used if the state of the gaze direction is required at a timestamp different from the recorded states.

Some implementations disclosed herein apply pulsed light and frequency-based segmentation to assess a pupil.

Segmenting in frequency space is robust to static source of noise and may be accomplished with relatively little computational cost and power. In some implementations, event cameras can facilitate the frequency segmentation by responding to flickering/pulsing light. In some implementations, the time intervals between two events are counted to provide a "frequency response" image, which may be automatically interpreted to identify pupil characteristics Some implementations utilize the retro-reflective property of the retina of the back of the eye (e.g., which historically are recognized as causing "red eye" and "bright pupil" effects). In some implementations, the light is pulsed at a frequency substantially different from the spectrum of frequencies of motion (for example, above the highest frequency in said motion) in the physical setting so that frequency-based segmentation can more easily be applied to distinguish reflections through the pupil from other reflections.

When a light source is almost coaxial (approximately on-axis illumination) with an image sensor, it "lights up" the pupil due to the retroreflective effect of the retina. This may be observed as the "red-eye" effect in photography and the "bright pupil" effect in IR light. Approximately on-axis illumination means that the light ray cast from the light source and the reflected ray coming from the retina are almost parallel to the camera optical axis.

FIG. 7 illustrates differences between a bright pupil effect and a dark pupil effect according to some implementations. In FIG. 7, a light source 705 is sufficiently far from the image sensor 710 such that the ray 728 cannot provide a reflection 726 off the retina 724 of the eye 720 that is captured by the image sensor 710. This off-axis illumination produces a normal dark pupil effect.

In contrast, where the light source 705 is sufficiently near the image sensor 705, the light source 705 produces a light ray 738 that provides a reflection 736 off the retina 724 of the eye 720 that is captured by the image sensor 710. This on-axis illumination produces a bright pupil effect of reflected light that has passed through the pupil 722 of the eye. The pattern of light reflected through the pupil 722 corresponds to the size, shape, and location of the pupil.

Approximately on-axis illumination can be achieved with a wave guide (e.g., a beam splitter). FIG. 8 illustrates use of a beam splitter 815 to provide approximately on-axis illumination. In this example, the light source 705 produces light that is reflected off the beam splitter 815 at an angle to provide a ray 836 that is parallel to the reflected ray 838 from the retina of the eye 720. The reflected ray 838 passes through the beam splitter and is captured by the image sensor 710. A beam splitter may be used to provide light that is perfectly on-axis, but at the potential cost of light loss (e.g., since light passes twice through the beam splitter, so only 25% of it may reach the image sensor). The same effect of rendering a virtual location of a light source to be substantially coaxial with the camera axis can be achieved using different types of waveguides, including using mirrors, fiber optics, diffractive optical elements, holographic elements, etc.

An alternative is illumination near or on top of the image sensor optics or as a ring around. FIG. 9 illustrates use of light source ring 905 near the optics 940 of a light sensor to provide approximately on-axis illumination. The lights source ring 905 is sufficiently close to the image sensor optics 940 such that, in the intended use cases (e.g., for the intended distances of the light source and image sensor from the eye), the axes are sufficiently aligned for light from the light source ring 905 to reflect off the retina of the eye 720 and be sensed by the image sensor 710. FIG. 10 illustrates the light source ring 905 around the image sensor optics 940.

Some implementations combine on-axis and off-axis illumination-based eye assessments. In some implementations, on-axis illumination is used to produce a bright pupil effect that is used to determine pupil characteristics and off-axis illumination is used to produce glints off the surface of the eye to determine other eye characteristics. Glints may be produced without interfering with the bright pupil frequency modulation by positioning them far enough from the image sensor axis. Pulsing the on-axis pupil illumination with a different frequency from the glint off-axis illumination may be used to distinguish them in the sensor data.

FIG. 11 illustrates a functional block diagram illustrating combining pupil detection based on on-axis illumination with eye characteristic detection based on off-axis illumination according to certain implementations. In this example, an on-axis light source (e.g., ring light source 905) is used in combination with an off-axis light source 1105. The on-axis light source (e.g., ring light source 905) is used to produce a bright pupil effect that is used to determine pupil characteristics and off-axis illumination is used to produce glints off the surface of the eye (e.g., glint 1110) to determine other eye characteristics.

FIG. 12 illustrates a collection of event camera data obtained during on-axis illumination. For example, events occurring within a given time period may be compiled and used to produce a frequency response image. FIG. 13 illustrates a close up view a portion of the event camera data of FIG. 12. In this example, the events in event grouping 1300 can be distinguished from the events in event grouping 1310 based on the frequency of the events. The system may determine that the events in event grouping 1300 are associated with the on-axis illumination based on the frequency and thus are indicative of a pupil's location, size, and shape. In contrast, the system may determine that the events in event grouping 1310 are not associated with the on-axis illumination and thus are not associated with the pupil. Event grouping 1310 may have been caused by the sun or another internal or external light source.

Numerous specific details are set forth herein to provide a thorough understanding of the claimed subject matter. However, those skilled in the art will understand that the claimed subject matter may be practiced without these specific details. In other instances, methods apparatuses, or systems that would be known by one of ordinary skill have not been described in detail so as not to obscure claimed subject matter.

Unless specifically stated otherwise, it is appreciated that throughout this specification discussions utilizing the terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provides a result conditioned on one or more inputs. Suitable computing devices include multipurpose microprocessor-based computer systems accessing stored software that programs or configures the computing system from a general purpose computing apparatus to a specialized computing apparatus implementing one or more implementations of the present subject matter. Any suitable programming, scripting, or other type of language or combinations of languages may be used to implement the teachings contained herein in software to be used in programming or configuring a computing device.

Implementations of the methods disclosed herein may be performed in the operation of such computing devices. The order of the blocks presented in the examples above can be varied for example, blocks can be re-ordered, combined, and/or broken into sub-blocks. Certain blocks or processes can be performed in parallel.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or value beyond those recited. Headings, lists, and numbering included herein are for ease of explanation only and are not meant to be limiting.

It will also be understood that, although the terms "first," "second," etc. may be used herein to describe various elements, these elements should not be limited by these terms. These terms are only used to distinguish one element from another. For example, a first node could be termed a second node, and, similarly, a second node could be termed a first node, which changing the meaning of the description, so long as all occurrences of the "first node" are renamed consistently and all occurrences of the "second node" are renamed consistently. The first node and the second node are both nodes, but they are not the same node.

The terminology used herein is for the purpose of describing particular implementations only and is not intended to be limiting of the claims. As used in the description of the implementations and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

The foregoing description and summary of the invention are to be understood as being in every respect illustrative and exemplary, but not restrictive, and the scope of the invention disclosed herein is not to be determined only from the detailed description of illustrative implementations but according to the full breadth permitted by patent laws. It is to be understood that the implementations shown and described herein are only illustrative of the principles of the present invention and that various modification may be implemented by those skilled in the art without departing from the scope and spirit of the invention.

What is claimed is:

1. A method comprising:

at an electronic device having a processor:

producing pulsed light at a frequency via a light source, the frequency corresponding to pulsing of the pulsed light;

receiving sensor data at a sensor;

identifying a subset of the sensor data corresponding to reflections of the pulsed light off a retina and through a pupil of an eye, wherein identifying the subset of the sensor data comprises distinguishing sensor data corresponding to reflections of the pulsed light from sensor data corresponding to reflections of light from another light source by identifying light pulses that occur at the frequency in the sensor data; and determining a pupil characteristic based on the subset of the sensor data corresponding to the reflections of the pulsed light off the retina and through the pupil of the eye.

2. The method of claim 1, wherein the sensor is an event camera and the subset of the sensor data corresponding to reflections of the pulsed light is identified by determining amounts of time between events and determining whether the events correspond to reflections of the pulsed light based on the amounts of time and the frequency.

3. The method of claim 1, wherein the sensor is a frame-based camera that captures images and the subset of the sensor data corresponding to reflections of the pulsed light is identified by subtracting the images from one another to identify light pulses at the frequency.

4. The method of claim 1, wherein the pulsed light is infrared (IR) light.

5. The method of claim 1, wherein the light source is aligned on axis with an optical axis of the sensor.

6. The method of claim 1, wherein an angle between a direction of light from the light source and an optical axis of the sensor is less than 15 degrees.

7. The method of claim 6, wherein the light source has an image generated by a wave-guide and produces on axis illumination.

8. The method of claim 7, wherein the on-axis illumination is produced via the light source being sufficiently near optics of the sensor such that the light source produces a light ray that provides a reflection off the retina of the eye that is captured by the optics of sensor.

9. The method of claim 7, wherein the on-axis illumination is produced via a light source ring around optics of the sensor.

10. The method of claim 1, wherein the frequency is greater than an object motion frequency threshold.

11. The method of claim 1 further comprising determining a gaze direction based on the pupil characteristic.

12. The method of claim 11, wherein the gaze direction is determined based on an ellipse corresponding to a shape of a pupil determined based on the sensor data.

13. The method of claim 11, wherein the gaze direction is determined based on one or more glints of light reflected from a second light source off a cornea surface of the eye.

14. The method of claim 1, wherein the pupil characteristic is pupil perimeter, pupil contour, pupil shape, or pupil center.

15. The method of claim 1, wherein the electronic device is a mobile device.

16. The method of claim 1, wherein the electronic device is a head-mounted device (HMD).

17. A non-transitory computer-readable storage medium, storing program instructions computer-executable on a computer to perform operations comprising:

producing pulsed light at a frequency via a light source, the frequency corresponding to pulsing of the pulsed light;

receiving sensor data at a sensor;

identifying a subset of the sensor data corresponding to reflections of the pulsed light off a retina and through a pupil of an eye, wherein identifying the subset of the sensor data comprises distinguishing sensor data corresponding to reflections of the pulsed light from sensor data corresponding to reflections of light from another light source by identifying light pulses that occur at the frequency in the sensor data; and determining a pupil characteristic based on the subset of the sensor data corresponding to the reflections of the pulsed light off the retina and through the pupil of the eye.

18. A device comprising:

a processor; and a computer-readable storage medium comprising instructions that upon execution by the processor cause the device to perform operations, the operations comprising:

producing pulsed light at a frequency via a light source, the frequency corresponding to pulsing of the pulsed light;

receiving sensor data at a sensor;

identifying a subset of the sensor data corresponding to reflections of the pulsed light off a retina and through a pupil of an eye, wherein identifying the subset of the sensor data comprises distinguishing sensor data corresponding to reflections of the pulsed light from sensor data corresponding to reflections of light from another light source by identifying light pulses that occur at the frequency in the sensor data; and determining a pupil characteristic based on the subset of the sensor data corresponding to the reflections of the pulsed light off the retina and through the pupil of the eye.

* * * * *